United States Patent
Lawson et al.

(10) Patent No.: US 6,612,173 B2
(45) Date of Patent: Sep. 2, 2003

(54) STEPPED PLUNGER FOR USE WITH AN ULTRASONIC SENSOR

(75) Inventors: Rebecca A. Lawson, Florence, SC (US); James W. Lowry, Florence, SC (US)

(73) Assignee: Sonoco Development, Inc., Hartsville, SC (US)

( * ) Notice: Subject to any disclaimer, the term of this patent is extended or adjusted under 35 U.S.C. 154(b) by 0 days.

(21) Appl. No.: 10/065,500

(22) Filed: Oct. 24, 2002

(65) Prior Publication Data

US 2003/0110861 A1 Jun. 19, 2003

Related U.S. Application Data

(60) Provisional application No. 60/339,074, filed on Dec. 12, 2001.

(51) Int. Cl.$^7$ ............................................... G01N 29/04
(52) U.S. Cl. ..................... 73/627; 73/1.73; 73/1.79; 73/290 R; 73/629
(58) Field of Search ..................... 73/627, 1.73, 1.74, 73/1.79, 290 R, 861.24, 861.25, 861.18, 861.06; 347/7; 367/99

(56) References Cited

U.S. PATENT DOCUMENTS

| | | | |
|---|---|---|---|
| 3,795,137 A | * 3/1974 | Lo et al. ..................... 73/45.4 |
| 3,798,959 A | * 3/1974 | Bowles et al. ............... 73/37.5 |
| 4,435,989 A | * 3/1984 | Meyer et al. ............ 73/864.14 |
| 4,489,618 A | * 12/1984 | Meyer ..................... 73/864.16 |
| 5,103,728 A | * 4/1992 | Barney ........................ 101/364 |
| 5,627,380 A | * 5/1997 | Crowne ...................... 250/577 |
| 5,724,890 A | * 3/1998 | Deschner et al. ........... 101/366 |
| 5,774,136 A | * 6/1998 | Barbehenn et al. ............ 347/7 |
| 5,878,667 A | * 3/1999 | Ryan .......................... 101/366 |
| 6,192,797 B1 | * 2/2001 | Rea et al. .................... 101/202 |
| 6,363,783 B1 | * 4/2002 | Turner et al. ............. 73/290 R |
| 6,397,745 B2 | * 6/2002 | Koehler ....................... 101/366 |
| 6,419,351 B1 | * 7/2002 | Lawson et al. ............... 347/86 |

* cited by examiner

Primary Examiner—Hezron Williams
Assistant Examiner—Jacques Saint-Surin
(74) Attorney, Agent, or Firm—Bullwinkel Partners, Ltd.

(57) ABSTRACT

An improved plunger for fluid dispensing cartridges used in automated dispensing systems. The plunger helps control the reflection of ultrasonic signals used to sense the position of the plunger as it moves within the cartridge tube. The plunger has a convex bottom, ink-facing surface and a top surface comprising one or more flat, horizontal surfaces. In the preferred embodiment, the horizontal surfaces are concentric steps.

5 Claims, 4 Drawing Sheets

STEPPED PLUNGER FOR USE WITH AN ULTRASONIC SENSOR

CROSS REFERENCE TO RELATED APPLICATIONS

This patent claims the benefit of U.S. Provisional Application No. 60/339,074 having a filing date of Dec. 12, 2001.

BACKGROUND OF INVENTION

This patent relates to fluid dispensing cartridges for automated dispensing systems, such as ink dispensing cartridges used with high-speed lithographic printing presses. More specifically, this patent relates to an improved plunger that helps control the reflection of ultrasonic signals used to sense the position of the plunger as it moves within the cartridge tube.

Typical lithographic ink cartridges comprise a hollow cylindrical body, a plunger and a dispensing fitment. The cylindrical body holds a supply of extrudable ink or varnish and has a dispensing end and a plunger end. The dispensing end is sealed with the dispensing fitment, which typically includes a nozzle for directing the flow of the ink. The plunger end is sealed by the plunger, which moves within the cylindrical body in response to pneumatic or other pressure to extrude ink out the nozzle.

Monitoring the level of ink in the cartridge is desirable for two reasons. First, it is necessary to know when the ink cartridge is empty and requires replacing. Second, it is desirable to know how much ink is being used for a particular printing job.

One method for determining the level of the ink in the cartridge involves sending a series of ultrasonic signals toward the plunger from a source mounted in the top of the automatic dispensing system and receiving reflected signals back. The reflected signals are processed to determine the level of the plunger and, concomitantly, the level of the ink in the cartridge body.

Conventional plungers for lithographic ink cartridges are made of plastic and are substantially cup-shaped. The plunger typically comprises a planar bottom wall and a sidewall extending upward from the periphery of the planar bottom wall. As the plunger is forced through the cartridge body by pneumatic pressure, the planar bottom wall pushes against the ink, causing it to be expelled through the dispensing fitment nozzle.

Due to the high viscosity of the ink and the tendency of certain fast drying inks to adhere the plunger sidewalls to the cartridge body, very high pressures are sometimes needed to advance the plunger. It has been found beneficial to mold stiffening ribs into the backside of the planar bottom wall to minimize twisting and distortion of the plunger when it is being subjected to high pressures.

Unfortunately, these stiffening ribs can interfere with the reflection of the ultrasonic signals, preventing an accurate reading of the ink level. This is because the height of the ribs often varies along their length and in places exceeds that which would allow an accurate reading of the plunger position using ultrasonic signals. A further problem is caused if the ribs are not identical. To alleviate the problems presented by the stiffening ribs, a disk having a flat reflecting surface may be placed behind the plunger, but this solution entails added cost.

The conventional "flat" plunger described above has an additional disadvantage in that it has a tendency to trap air inside the cartridge body. After the cartridge has been filed with ink and the plunger inserted into the cartridge, air can become trapped underneath the plunger. Ink contacting the air can dry out over time. If the dried ink is expelled from the cartridge, it can create printing defects such as hickies.

The problem of air entrapment can be minimized or eliminated by using a plunger having a convex surface facing the ink, such as that disclosed in Lawson et al. U.S. Pat. No. 6,419,351. The convex shape facilitates the flow of air away from the center of the plunger and toward the cartridge body wall when the plunger is inserted into the filled cartridge and pressed against the ink. To further aid the flow of air away from the center of the plunger, the bottom surface of the plunger may be textured with bumps, nubs, ridges, grooves or any other type of projection or indentation capable of defining channels through which air can flow when the plunger comes into contact with the ink.

The convex plunger disclosed in the '351 patent has a corresponding concave upper surface. When such a plunger is used with ultrasonic sensors, the concave upper surface cancels out the ultrasonic signal, causing an error reading. To alleviate this problem, the convex plunger may be molded with a flat backside to better reflect ultrasonic signals, but this solution entails added material and cost. Furthermore, molding a convex plunger with a flat backside results in an unacceptably longer cycle (manufacturing) time due to the additional time needed to cool the extra thermoplastic material contained in the newly molded plunger.

Thus it is an object of the present invention to provide a convex plunger that enables proper reflection of ultrasonic signals used to sense the position of the plunger as it moves within the cartridge tube.

Further and additional objects will appear from the description, accompanying drawings, and appended claims.

SUMMARY OF INVENTION

The present invention is an improved plunger for fluid dispensing cartridges that helps control the reflection of ultrasonic signals used to sense the position of the plunger as it moves within the cartridge tube. In one anticipated application, the plunger is used in ink cartridges for high-speed lithographic printing systems. The plunger bottom wall has a convex bottom (fluid facing) surface and a top surface having a reflective area comprising one or more flat, horizontal surfaces. In the preferred embodiment, the horizontal surfaces are concentric steps of equal height.

DETAILED DESCRIPTION

Figure 1:
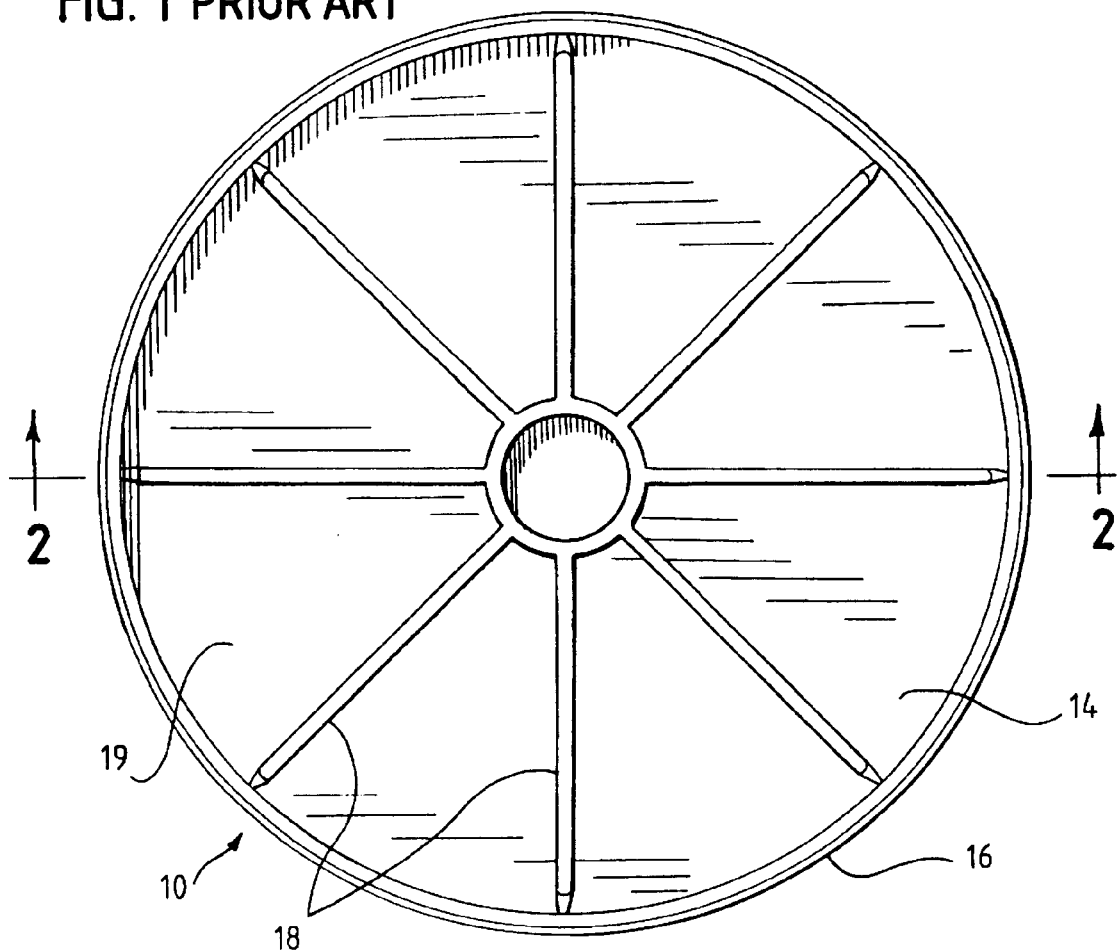
FIG. 1 is a top plan view of a conventional flat surface plunger.
Figure 2:
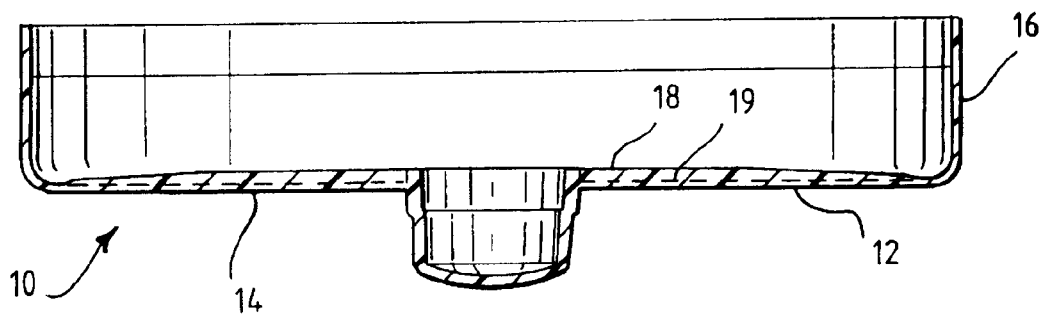
FIG. 2 is a cross-sectional view of the conventional flat surface plunger of FIG. 1 taken along line 2—2.

Turning to the drawings, there is shown in FIGS. 1 and 2 a conventional lithographic ink cartridge plunger 10 having a flat bottom (ink facing) surface 12. The plunger 10 is substantially cup-shaped, comprising a bottom wall 14 and a sidewall 16 extending upward from the periphery of the bottom wall 14. As the plunger 10 travels through the cartridge body, such as the one shown in FIG. 7, the flat bottom surface 12 pushes against the ink, causing it to be expelled through a nozzle. Stiffening ribs 18 have been molded into the backside 19 of the bottom wall 14 to minimize twisting and distortion of the plunger 10 when it is being subjected to high pressures.

As perhaps best shown in FIG. 2, the vertical height of the ribs 18 varies along their length, which can result in an inaccurate reading of the plunger position using an ultrasonic signal. A disk (not shown) having a flat reflecting surface may be placed behind the plunger 10 and over the ribs 18, but this entails added cost.

The plunger 10 of FIGS. 1 and 2 has a tendency to trap air inside the cartridge body between the flat surface 12 of the bottom wall 14 and the top surface of the ink. This problem of air entrapment can be minimized or eliminated by using a plunger having a convex ink-facing surface.

Figure 3:
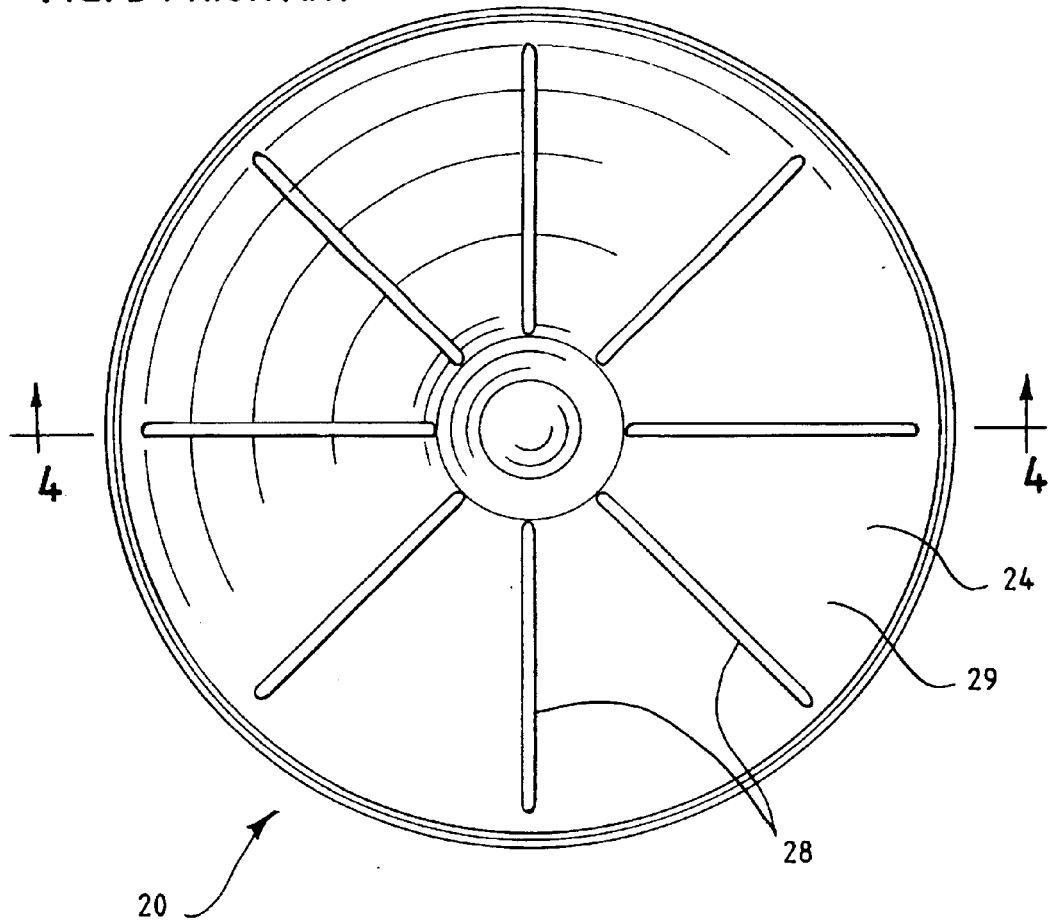
FIG. 3 is a top plan view of a convex surface plunger.
Figure 4:
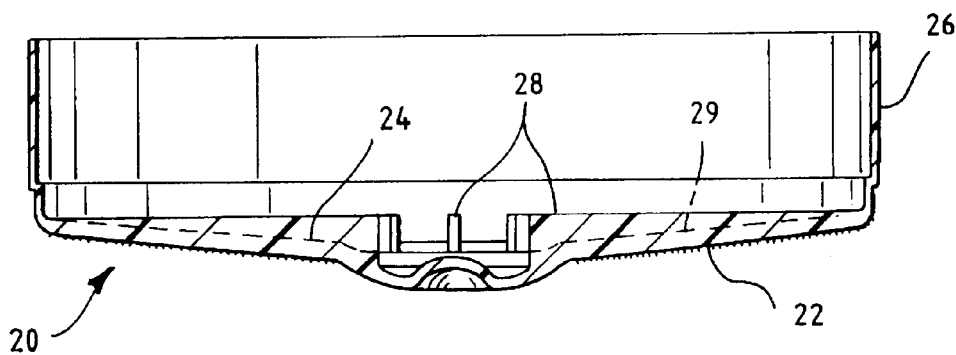
FIG. 4 is a cross-sectional view of the convex surface plunger of FIG. 3 taken along line 4—4.

FIGS. 3 and 4 show a plunger having a convex ink-facing surface. The plunger 20 comprises a bottom wall 24 and a sidewall 26 extending upward from the periphery of the bottom wall 24. The bottom wall 24 has a convex bottom (ink-facing) surface 22 whose convex shape facilitates the flow of air away from the center of the bottom wall 24 and toward the cartridge body wall when the plunger 20 is inserted into the filled cartridge and pressed against the ink. To further aid the flow of air away from the center of the plunger 20, the bottom surface 22 may be textured with bumps, nubs, ridges, grooves or any other type of projection or indentation capable of defining channels through which air can flow when the plunger comes into contact with the ink. The convex plunger 20 may be molded with stiffening ribs 28 extending upward from the top surface 29 of the bottom wall in order to strengthen the plunger and prevent twisting during use.

When used with ultrasonic sensors, the concave top surface 29 cancels out the ultrasonic signal, causing an error reading. While the convex plunger 20 may be molded with a flat backside to better reflect ultrasonic signals, this solution entails added material and cost. Furthermore, molding a convex plunger with a flat backside results in an unacceptably longer cycle (manufacturing) time due to the additional time needed to cool the additional thermoplastic material contained in the molded plunger.

Figure 5:
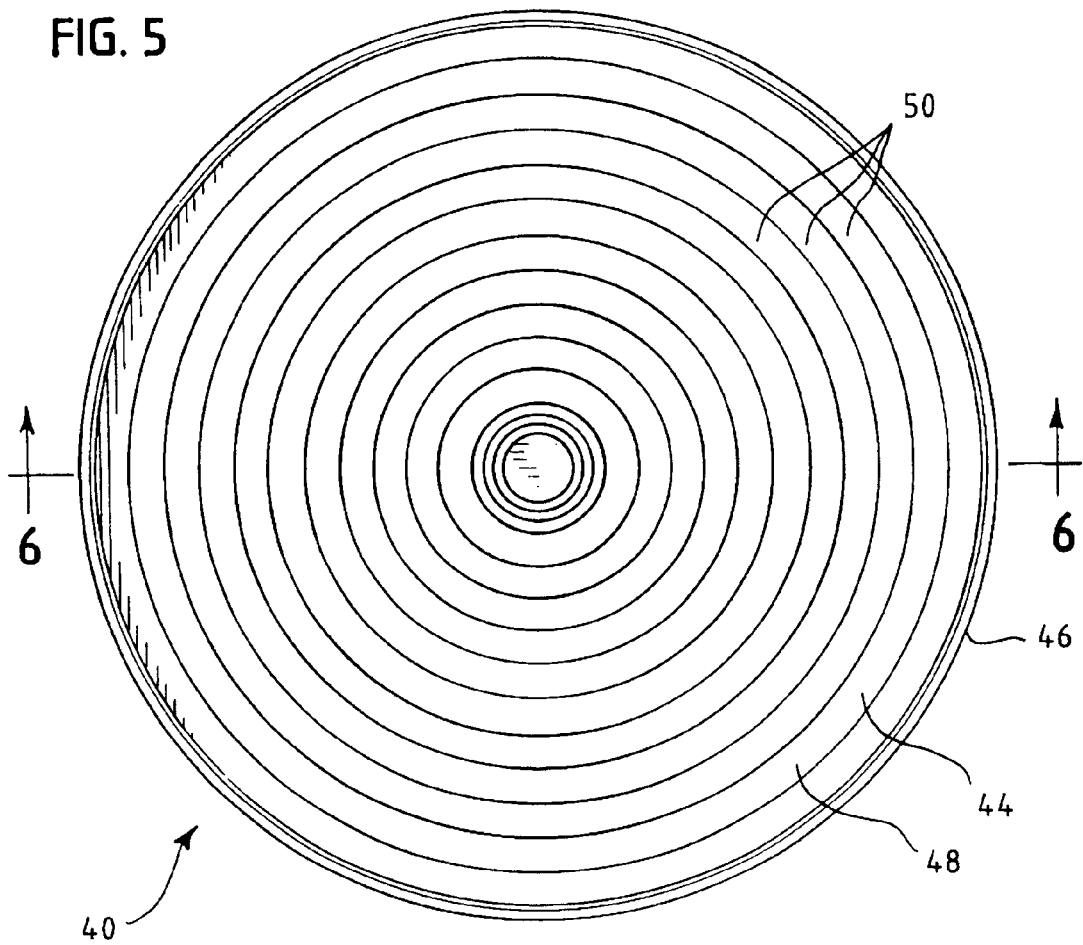
FIG. 5 is a top plan view of a stepped plunger according to the present invention.
Figure 6:
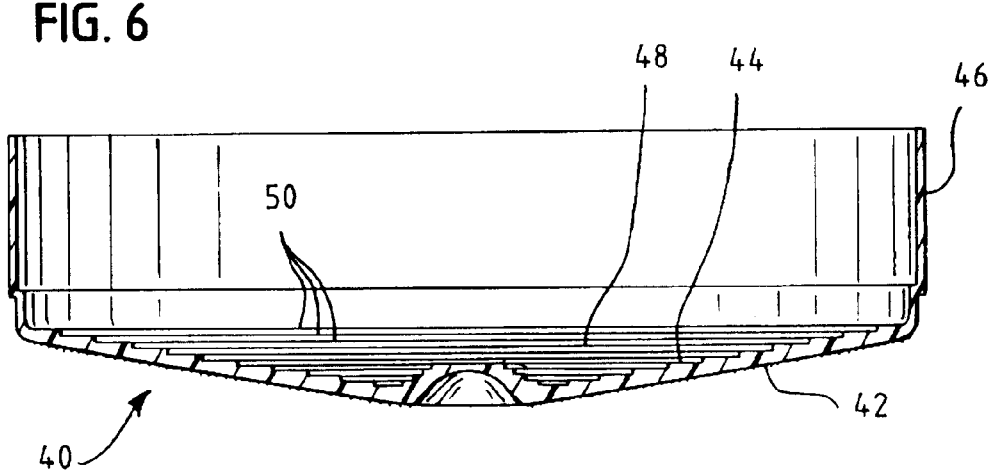
FIG. 6 is a cross-sectional view of the stepped plunger of FIG. 5 taken along line 6—6.

The present invention is a convex plunger that enables proper reflection of ultrasonic signals used to sense the position of the plunger as it moves within the cartridge tube. One embodiment of the present invention, a stepped plunger 40 for use in a high-speed lithographic printing system, is shown in FIGS. 5 and 6. The stepped plunger 40 is substantially cup-shaped and comprises a bottom wall 44 and a sidewall 46 extending upward from the periphery of the bottom wall 44. The bottom, ink-facing surface 42 of the bottom wall 44 is convex to facilitate the flow of air away from the center of the plunger 40 when the plunger 40 is inserted into the ink-filled cartridge and pressed against the ink. The bottom surface 42 may be textured with bumps, nubs, ridges and grooves or have other means for channeling air outward from the center of the plunger bottom wall 44 toward the sidewall 46.

The top surface 48 of the plunger bottom wall 44 comprises a reflective area against which the ultrasonic signals reflect during operation of the fluid dispensing system. The reflective area comprises one or more flat, horizontal surfaces that reflect ultrasonic signals from a source located above the plunger 40 back to a receiver. The receiver sends the signals to a processing unit where they are processed in order to determine the level of the plunger, and thus the level of ink or other fluid in the cartridge. The source of the ultrasonic signals and the receiver may be a single unit, hereinafter referred to as the "sensor" or "ultrasonic sensor".

Preferably, the reflective area comprises a series of circular steps 50 arranged concentrically about a center point, which preferably coincides with the center point of the plunger 40. Each step 50 has a horizontal upper surface capable of reflecting an ultrasonic signal back to the sensor. The height of the steps 50 can vary from step to step, but the height of any one step 50 should be constant and be a multiple of a given variable, the value of which is a function of the type of ultrasonic sensor used and the wavelength of the signal at that sensor's frequency. Preferably, the steps 50 are the same height. The number of steps 50 is a function of step height and plunger geometry.

The steps 50 serve two primary functions. First, they eliminate the need for stiffening ribs. Second, their flat top surfaces reflect the ultrasonic signals used to sense the position of the plunger 40 as it moves within the cartridge tube.

Although the top surface 48 of the plunger bottom wall 44 has been described as comprising concentric circular steps 50, the top surface 48 could have any shape and configuration that provides one or more flat, horizontal surfaces whose relative heights are a function of the type of ultrasonic sensor and the signal frequency.

Alternatively, the top surface 48 could comprise one or more flat, horizontal surfaces in the region of the plunger where the ultrasonic signals strike, and a non-flat, non-horizontal surface elsewhere. Regardless of the shape and configuration of the plunger bottom wall top surface 48, it is desirable that the shape and configuration exhibit axial symmetry so that the cartridge and plunger can be installed in the automatic dispensing system without regard to rotational orientation.

The stepped plunger 40 is most useful in larger diameter cartridges such as that described in U.S. Pat. No. 6,192,797, incorporated herein by reference, but it may be used with any suitable cartridge or container in which ultrasonic signals reflecting off the top surface of the plunger are used to determine fluid level. The fluid may be ink, paint, varnish, a food product or any extrudable fluid.

Figure 7:
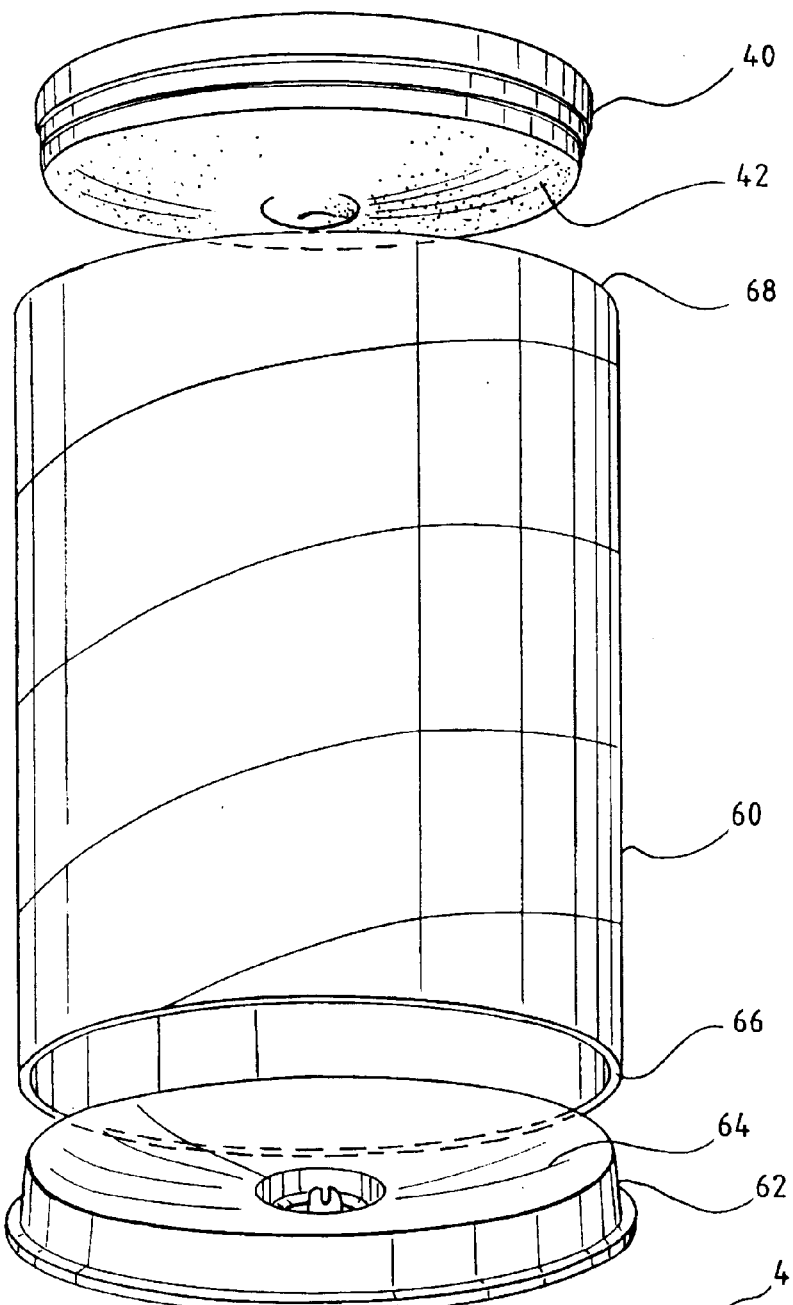
FIG. 7 is an exploded view of an ink cartridge assembly.
Figure 8:
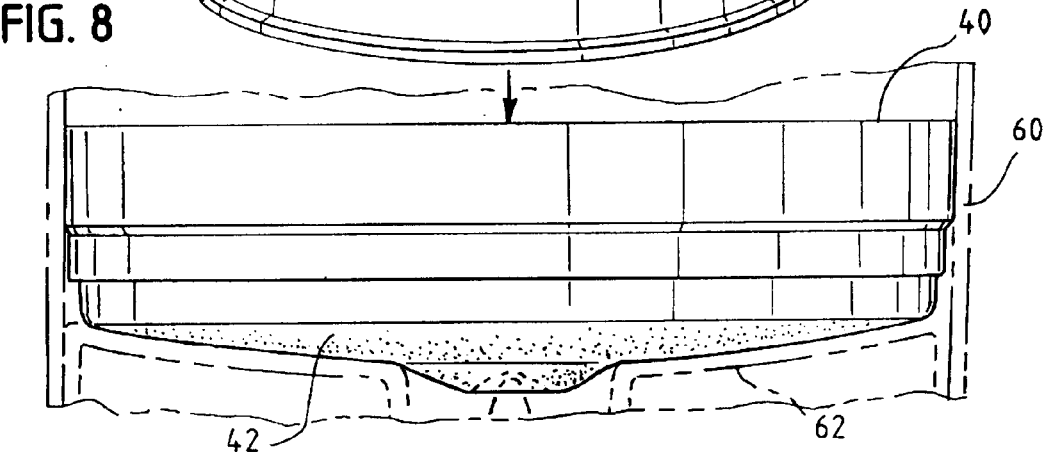
FIG. 8 is a side view of the convex plunger of FIG. 7 with the cartridge body and dispensing fitment shown in phantom lines.

FIGS. 7 and 8 show the plunger 40 as it might be used in a larger diameter ink cartridge. The cartridge comprises a hollow cylindrical body 60, the plunger 40 and a dispensing fitment 62. The cylindrical body 60 holds a supply of extrudable ink or varnish and has a dispensing end 66 and a plunger end 68. The dispensing end 66 is sealed with the dispensing fitment 62. The plunger end 68 is sealed by the plunger 40, which moves within the cylindrical body 60 in response to pneumatic or other pressure to extrude ink out the nozzle. The dispensing fitment 62 should have a concave top surface 64 that mates with the convex bottom surface 42 of the plunger to minimize unused ink after the plunger 40 has traveled the full length of the cartridge, as shown in FIG. 8.

Other modifications and alternative embodiments of the invention are contemplated which do not depart from the scope of the invention as defined by the foregoing teachings and appended claims. It is intended that the claims cover all such modifications that fall within their scope.

What is claimed is:

1. In an improved plunger for a fluid dispensing cartridge, the plunger comprising a bottom wall and a sidewall extending upward from the periphery of the bottom wall, the bottom wall having a convex ink-contacting surface, the position of the plunger being determined by a series of ultrasonic signals emitted from a sensor located above the plunger and reflected off the plunger back to the sensor, the improvement comprising:

the bottom wall having a top surface, the top surface comprising a reflective area upon which the ultrasonic signals reflect, the reflective area comprising one or more substantially flat, horizontal surfaces capable of reflecting the ultrasonic signals back to the sensor.

2. The plunger of claim 1 wherein the reflective area comprises a series of circular concentric steps, each step having a substantially horizontal upper surface capable of reflecting the ultrasonic signals back to the sensor.

3. The plunger of claim 2 wherein the height of each step is a multiple of a variable, the value of which is determined by the type of sensor and the sensor's frequency.

4. The plunger of claim 3 wherein the steps are of substantially equal height.

5. The plunger of claim 1 wherein the plunger sidewall is substantially cylindrical and defines a center axis and the reflective area exhibits axial symmetry about the axis.

\* \* \* \* \*